United States Patent [19]

Chaitin

[11] 4,090,501
[45] May 23, 1978

[54] SKIN LESION ANALYZER

[76] Inventor: Horace Chaitin, 6 Peppermill Rd., Roslyn, N.Y. 11576

[21] Appl. No.: 699,645
[22] Filed: Jun. 24, 1976
[51] Int. Cl.² .............................................. A61B 5/00
[52] U.S. Cl. ..................................... 128/2 H; 128/23
[58] Field of Search .............. 128/2 W, 2 H, 2 R, 23; 240/2 M, 2 MA; 350/114, 256, 237; 73/356, 359, 372

[56] References Cited

U.S. PATENT DOCUMENTS

| 2,389,282 | 11/1945 | Stegeman | 73/372 |
| 2,586,723 | 2/1952 | Sakols | 240/2 M |
| 2,795,997 | 6/1957 | Allen | 240/2 M |
| 3,546,778 | 12/1970 | Lepkowski | 350/114 |
| 3,661,142 | 5/1972 | Flam | 128/2 H |
| 3,774,614 | 11/1973 | Cook | 128/325 |

Primary Examiner—Robert W. Michell
Assistant Examiner—Michael H. Thaler
Attorney, Agent, or Firm—Joel F. Spivak

[57] ABSTRACT

A medical appliance useful for the detection and analysis of skin lesions consists of a magnifier having a flat bottom surface and a scale in combination therewith, the magnifier being mounted on a frame which includes a vertically extending metal rod having a light source attached thereto.

2 Claims, 4 Drawing Figures

U. S. Patent  May 23, 1978  4,090,501
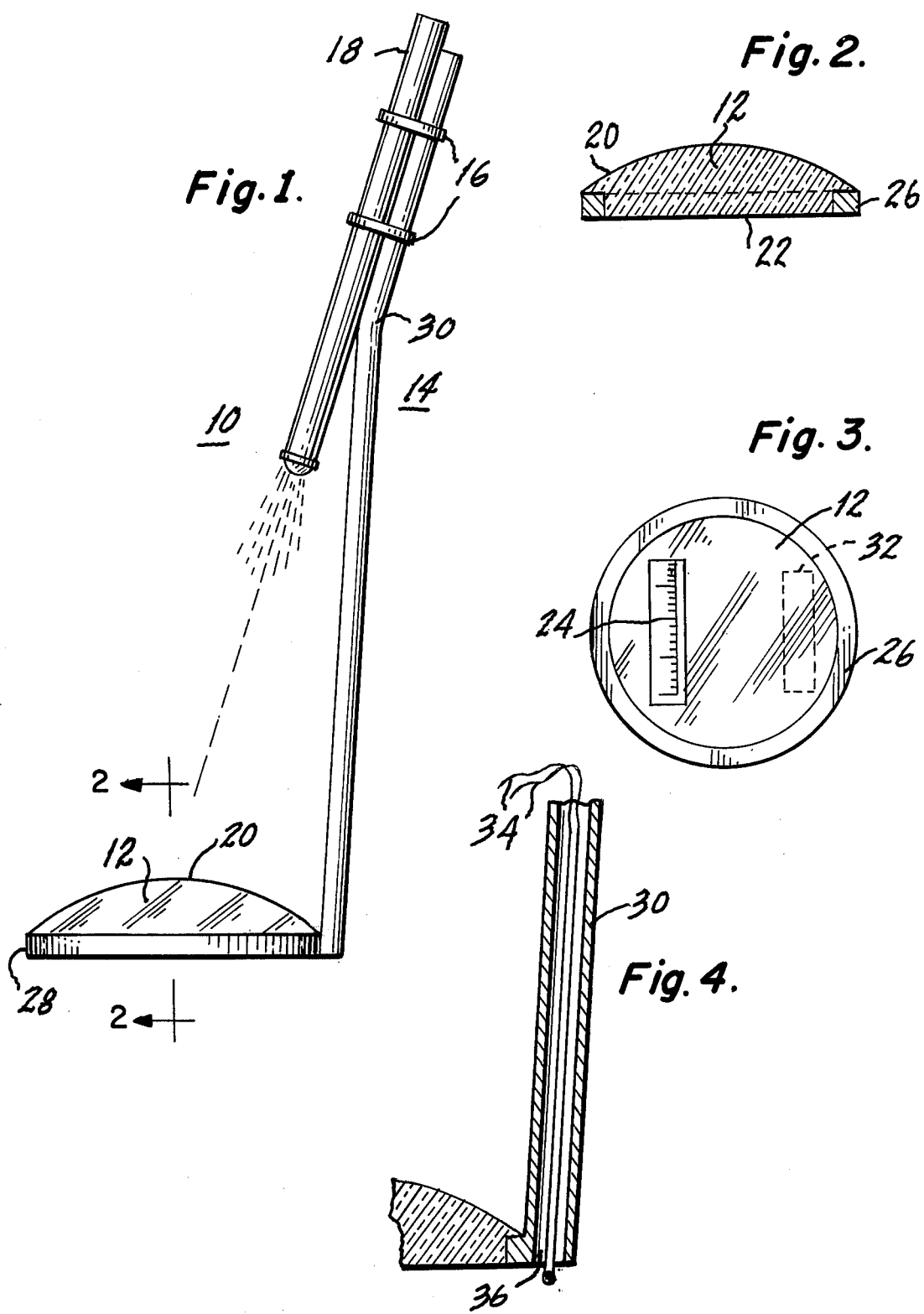

SKIN LESION ANALYZER

BACKGROUND OF THE INVENTION

The present invention deals with medical appliances and, in particular an appliance useful for the examination and detection of skin lesions.

Skin lesions (abnormal areas of the skin) are caused by different types of pathology. For example, skin lesions can be in the form of small areas of hemmorrhage, collections of small blood vessels forming a skin tumor, deposition of varying types and amounts of pigment, scales, ulcerated conditions, and inflammatory reactions with the dilatation of blood vessels. There may be varying levels of elevation of the lesion above the natural level of skin.

At present, the time honored procedure for analyzing or examining the above lesions is for the physician to apply finger pressure on the lesion and then remove the pressure suddenly to see if the area changes character. It is often found that the change in character associated with many lesions can be so rapid and subtle so as to make detection difficult.

I have therefore, developed an instrument which can be placed directly on the lesion with pressure and the changes seen as they occur without having to remove the instrument. The instrument further makes the changes more readily visible and allows the physician to measure the size of the lesion.

SUMMARY OF THE INVENTION

An apparatus useful for detecting and analyzing skin lessions comprising magnifying means having a flat bottom surface and a reticle associated therewith. The magnifying means is mounted on a frame having a rod extending vertically from the bottom portion of the frame. Means for mounting a light source on the rod directing light on to the area of the magnifier is included with the apparatus.

BRIEF DESCRIPTION OF THE DRAWINGS

FIG. 1 is a side elevational view of an embodiment of the invention.

FIG. 2 is a cross-sectional view of the magnifier and the base of the frame of the embodiment shown in FIG. 1 as taken through 2—2.

FIG. 3 is a bottom elevational view of the magnifying element of FIG. 1.

FIG. 4 is a cross-sectional view of an embodiment of a handle useful in the apparatus.

DETAILED DESCRIPTION OF THE INVENTION

Referring to the figure there is shown a skin lesion diagnostic apparatus 10 which includes magnifying means 12, mounted on a frame 14. The frame 14 includes means 16 for mounting a light source 18 thereon.

The magnifier means 12 as shown, consists of a glass or plastic magnifying element having a convex upper surface 20 and a flat lower surface 22. A reticle 24 may be etched or otherwise formed on the flat lower surface 22 of the magnifier 12. This reticle will enable the physician to easily measure the size of any lesion. The lower periphery of the magnifier 12 is formed with a lip or flange 26 for seating the magnifier 12 on the frame 14.

The frame 14 has a lower circular ring member 28 formed with a flat top surface such that the lip or flange 26 of the magnifier will seat thereon so as to be supported thereby. Alternatively the magnifier could be formed with a circular groove in its bottom surface for seating the ring 28. Preferably the magnifier is glued to the ring 28. The thickness of the ring 28 is preferably the same as or less than the thickness of the lip or flange 26 of the magnifier 12 so that the magnifier 12 will have contact with the skin during use. The frame 14 also has a handle 30 extending upwardly from the ring 28 and attached to or part of the ring 28 at the lower end of the handle 30.

The handle 30 preferably is slightly tilted from the vertical position for ease of viewing. The upper portion of the handle 30 is provided with a pair of spring clips 16 for accepting and holding a light source 18, such as a pen light, in position. The light source 18 provides light over the area of the suspected lesions.

As another option and diagnostic tool, the apparatus 10 can provide means for measuring the temperature of the skin. Since the area associated with a lesion generally exhibits a higher skin temperature as compared with surrounding areas, such an addition can be of great value.

Temperature measuring means can be provided by a thin film 32 of a cholesteric liquid crystal composition hermetically sealed to the flat bottom surface of the magnifier 12. The particular composition used is chosen so as to exhibit color changes in the temperature region generally exhibited by the surface of the body. Such compositions are known in the art.

An alternate means for temperature measurement is shown with reference to FIG. 4. Referring to the Figure, the handle 30 is hollow and is provided with a thermocouple 34 extending therethrough and terminating slightly below its open lower end 36. The thermocouple wires are then connected to a voltmeter calibrated in degrees for direct temperature read out.

What I claim is:

1. An apparatus useful for the diagnosis and analysis of skin lesions consisting of a single magnifier for magnifying the image of said skin lesion, said magnifier having a flat bottom surface mounted on a frame, a handle extending upwardly from said frame and having an external light source holding means attached thereto and temperature detection means comprising a cholesteric liquid crystal composition capable of altering color in a predictable manner according to variations in surface body heat, said composition being contained on said flat bottom surface of said magnifier.

2. An apparatus useful for the diagnosis and analysis of skin lesions consisting of a single magnifier for magnifying the image of said skin lesion, said magnifier having a flat bottom surfact mounted on a frame, a handle extending upwardly from said frame and having an external light source holding means attached thereto and temperature detection means comprising a thermocouple, said thermocouple being held within said handle, said handle being a hollow rod.

* * * * *